United States Patent [19]
Lee et al.

[11] Patent Number: 5,650,176
[45] Date of Patent: Jul. 22, 1997

[54] SYNTHESIS OF REACTIVE AMORPHOUS CALCIUM PHOSPHATES

[75] Inventors: Dosuk D. Lee, Brookline, Mass.; Christian Rey, Castanet, France; Maria Aiolova, Brookline, Mass.

[73] Assignee: Etex Corporation, Cambridge, Mass.

[21] Appl. No.: 581,179

[22] Filed: Dec. 29, 1995

Related U.S. Application Data

[62] Division of Ser. No. 446,182, May 19, 1995.

[51] Int. Cl.$^6$ .................................................. C01B 25/32
[52] U.S. Cl. ........................... 424/602; 423/308; 423/311; 514/2
[58] Field of Search .................... 423/308, 311; 514/2; 424/602

[56] References Cited

U.S. PATENT DOCUMENTS

| | | |
|---|---|---|
| Re. 33,161 | 2/1990 | Brown et al. |
| Re. 33,221 | 5/1990 | Brown et al. |
| 4,612,053 | 9/1986 | Brown et al. |
| 4,737,411 | 4/1988 | Graves, Jr. et al. |
| 4,849,193 | 7/1989 | Palmer et al. |
| 4,880,610 | 11/1989 | Constantz |
| 4,917,702 | 4/1990 | Scheicher et al. |
| 4,938,938 | 7/1990 | Ewers et al. ........................ 423/311 |
| 4,959,104 | 9/1990 | Iino et al. |
| 5,037,639 | 8/1991 | Tung |
| 5,053,212 | 10/1991 | Constantz et al. |
| 5,129,905 | 7/1992 | Constantz |
| 5,149,368 | 9/1992 | Liu et al. |
| 5,178,845 | 1/1993 | Constantz et al. |
| 5,336,264 | 8/1994 | Constantz et al. |
| 5,470,803 | 11/1995 | Bonfield et al. ...................... 423/308 |
| 5,496,399 | 3/1996 | Ison et al. |
| 5,522,893 | 6/1996 | Chow et al. |
| 5,525,148 | 6/1996 | Chow et al. |
| 5,542,973 | 8/1996 | Chow et al. |
| 5,545,254 | 8/1996 | Chow et al. |

FOREIGN PATENT DOCUMENTS

| | | |
|---|---|---|
| 63-170205 | 7/1988 | Japan. |
| WO94/02412 | 2/1994 | WIPO. |

OTHER PUBLICATIONS

Besic et al., "Electron probe microanalysis of noncarious enamel and dentin and calcified tissues in mottled teeth", J. Dent. Res., 48:131, 1969.

Constantz et al., "Skeletal repair by in situ formation of the mineral phase of bone", Science, 267:1976, 1995.

Eanes et al., "Intermediate states in the precipitation of hydroxyapatite", Nature, vol. 208, pp. 365–367, Oct. 23, 1965.

Eanes, "Thermochemical studies on amorphous calcium phosphate", Calc. Tiss. Res., 5:133, 1970.

Glimcher et al., "Recent studies of bone mineral: Is the amorphous calcium phosphate theory valid?", Jour. of Crystal Growth, 53:100–119, 1981.

Holmes et al., "Surface areas by gas adsorption on amorphous calcium phosphate and crystalline hydroxyapatite", Calc. Tiss. Res., 7:163, 1971.

Labarthe et al., "Sur la structure et les proprietes des apatites carbonatees de type B phospho–calciques", Ann. Chem., 8:289, 1973.

Nylen et al., "Molecular and ultrastructural studies of non–crystalline calcium phosphates", Calc. Tiss. Res., 9:95, 1972.

(List continued on next page.)

*Primary Examiner*—Wayne Langel
*Attorney, Agent, or Firm*—Choate, Hall & Stewart

[57] ABSTRACT

The present invention provides a novel process for converting a standard inert amorphous calcium phosphate precipitate into highly reactive amorphous solids. The amorphous solids can be used to react with other calcium phosphate solids to form a poorly-crystalline synthetic hydroxyapatite that provides both bioactivity and structural integrity. This novel amorphous material can be reacted with other calcium phosphates at or below 37° C. to form a bone-like material consisting of poorly crystalline hydroxyapatite.

8 Claims, 4 Drawing Sheets

OTHER PUBLICATIONS

Pool, "Coral chemistry leads to human bone repair", Science, 269:1772 (Mar., 1995).

Posner et al.,"Synthetic amorphous calcium phosphate and its relation to bone mineral structure", Bone Mineral Structure, vol. 8, pp. 273–281, 1975.

Rey et al., "The carbonate environment in bone mineral: a resolution–enhanced fourier transform infrared spectroscopy study", Calcif. Tissue Int., 45:157, 1989.

Rey et al., "Structural studies of the mineral phase of calcifying cartilage", J. Bone Min. Res., 6:515, 1991.

Rey et al., "Preparation of Microporous Ceramic at Low Temperature from Poorly Crystalline Apatite" *Symposium Abstract*, 1993.

Tung et al., "An intermediate state in hydrolysis of amorphous calcium phosphate", Calcif. Tissue Int., 35:783, 1983.

Blumenthal et al., *Mat. Res. Bulletin*, 7(11), pp. 1181–1189 (Nov. 1972).

*Chemical Abstracts*, 108(10), p. 166, No. 78193h (Mar. 7, 1988).

*Chemical Abstracts*, 113(24), p. 386, No. 218168j (Dec. 10, 1990).

Chemical Abstracts 77:15878 (1972).

(a)

(b)

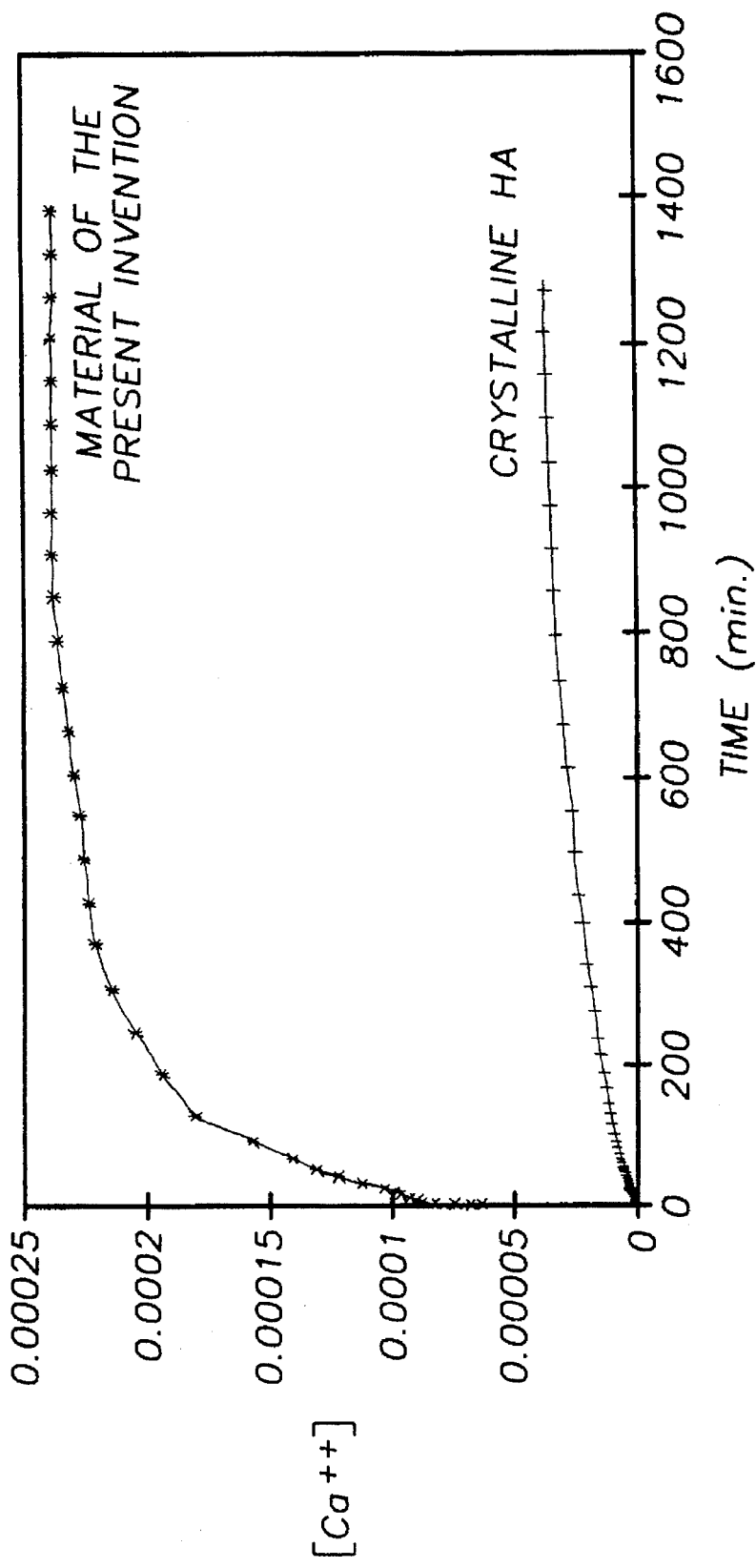

SYNTHESIS OF REACTIVE AMORPHOUS CALCIUM PHOSPHATES

This is a divisional of application Ser. No. 08/446,182 filed on May 19, 1995 pending.

FIELD OF THE INVENTION

This invention relates to a synthetic poorly-crystalline hydroxyapatite useful as human or animal implant material and for other purposes. The invention further relates to synthesis of amorphous phosphate compounds useful in the formation of poorly-crystalline hydroxyapatite at low temperatures.

BACKGROUND OF THE INVENTION

Calcium phosphates are the principal constituent of hard tissues (bone, cartilage, tooth enamel and dentine). Naturally-occurring bone mineral is made of nanometer-sized, poorly-crystalline calcium phosphate with hydroxyapatite structure. However, unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae,

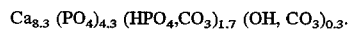

$Ca_{8.3}(PO_4)_{4.3}(HPO_4,CO_3)_{1.7}(OH,CO_3)_{0.3}$.

Bone mineral non-stoichiometry is primarily due to the presence of divalent ions, such as $CO_3^{2-}$ and $HPO_4^{3-}$ which are substituted for the trivalent $PO_4^{3-}$ ions. Substitution by $HPO_4^{3-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones.

It is the Ca/P ratio in conjunction with nanocrystalline size and the poorly-crystalline nature that yields specific solubility property of the bone minerals. And because bone tissues undergo constant tissue repair regulated by the mineral-resorbing cells (Osteoclasts) and mineral-producing cells (Osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autogenous bone (patient's own bone) and the risks and complications associated with allograft bone (bone from a cadaver), such as risks of viral transmission. Consequently, there has been considerable attempts to synthesize a ceramic material which closely resembles natural bone for use as implants. Hydroxyapatite is the preferred choice because, although it is a stoichiometric, crystalline form with generally larger crystal sizes, it is chemically closest to the naturally occurring mineral in bone.

An ideal synthetic bone graft should possess a minimum of following four properties: (1) it should be chemically biocompatible like hydroxyapatite; (2) it should provide some degree of structural integrity in order to keep the graft in place and intact until the patient's own bone heals around it; (3) it should be a soluble form to permit resorption so that the patient's own bone replace the foreign hydroxyapatite; and, (4) because it may be necessary to incorporate biomolecules, such as bone growth proteins that can stimulate bone-forming osteoblast cells, into the synthetic bone material, it is desirable that the process used to form the material be carried out at low temperatures. Most bone growth proteins (such as Bone Morphogenetic Proteins) are heat sensitive and lose their bioactivity at temperatures exceeding body temperatures.

Fulfillment of these requirements may be accomplished by a material in which parameters, such as Ca/P ratios, crystal size, crystallinity, porosity, density, thermal stability and material purity are controlled.

The prior art (LeGeros R. Z., in *Calcium Phosphates in Oral Biology and Medicine*, Karger Pub. Co., New York, 1991) teaches that highly crystalline form of hydroxyapatite is produced by solution precipitation followed by sintering at high temperatures (800°–1200° C.). High temperature treatment yields highly stoichiometric hydroxyapatite with crystal sizes on the order of several microns with Ca/P of 1.67. Such highly crystalline hydroxyapatite has an extremely low solubility rendering it essentially insoluble in the host tissue. Therefore, it is not replaced by living bone tissue and it remains intact in the patient for an undesirably extended period.

The prior art further teaches that hydroxyapatite is produced by a solid-state acid-base reaction of primarily crystalline calcium phosphate reactants. Such an approach results in materials that are sometimes poorly reacted, inhomogeneous and which have a significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, Constantz et al. U.S. Pat. No. 5,053,212 discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in *Science* (Vol. 267, pp. 1796–9 (24 Mar. 1995)) the formation of a carbonated apatite from the reaction of monocalcium phosphate monohydrate, Beta-tricalcium phosphate, Alpha-tricalcium phosphate, and calcium carbonate in a sodium phosphate solution, to provide a calcium phosphate material which is still substantially more crystalline in character than naturally occurring bone minerals.

Similarly, Brown et al. in U.S. Reissue No. 33,221 report on the reaction of crystalline tetracalcium phosphate (Ca/P of 2.0) with acidic calcium phosphates. Liu et al. in U.S. Pat. No. 5,149,368 discloses the reaction of crystalline calcium phosphate salts with an acidic citrate.

All of these prior art references discloses a chemical reaction resulting in crystalline form of hydroxyapatite solids that has been obtained by reacting crystalline solids of calcium phosphate. There has been little reported on the use of amorphous calcium phosphates (Ca/P of approximately 1.5) as one of the reactant because the amorphous calcium phosphates are the least understood solids among the calcium phosphates and the conventional amorphous calcium phosphate is largely considered to be inert and non-reactive solid.

The only mention of the amorphous calcium phosphate material in prior art has focused on the use of the amorphous calcium phosphate as a direct precursor to the formation of a highly crystalline hydroxyapatite compounds under generally high temperature treatments. Such a highly crystalline material is inappropriate for synthetic bone because it is highly insoluble under physiological conditions.

For example, Palmer et al. in U.S. Pat. No. 4,849,193 report the formation of crystalline hydroxyapatite powder by reacting an acidic calcium phosphate solution with a calcium hydroxide solution, with both solutions near saturation, so as to form an amorphous hydroxyapatite precipitate powder. The amorphous powder is then immediately dried and sintered at high temperature of 700°–1100° C. to obtain a very high crystalline hydroxyapatite. Brown et al. in U.S. Pat. No. Re 33,221 report on the formation of crystalline hydroxyapatite for dental cement by reacting an amorphous phase specifically restricted to tetracalcium phosphate (Ca/P of 2.0) with at least one of the more acidic calcium phosphates. Further, Brown et al., does not disclose the preparation or the properties of such a tetracalcium phosphate in amorphous state. Tung in U.S. Pat. No. 5,037,639 discloses the use and application of standard amorphous calcium phosphate paste for the remineralization of teeth. Tung proposes the use of standard inert amorphous calcium phosphate mixed with and delivered through as a chewing gum, mouth rinse or toothpaste, which upon entering oral fluids converts to crystalline fluoride containing hydroxyapatite which is useful to remineralize tooth enamel. Simkiss in PCT/GB93/01519 describes the use of inhibitors, such as Mg ions or pyrophosphate, mixed with amorphous calcium phosphate and implanted into living tissues. Upon leaching of, for example Mg ions, into surrounding bodily fluids, the amorphous calcium-magnesium phosphate converts into crystalline hydroxyapatite.

There remains a need to develop new synthetic bone material that more closely mimics the properties of naturally-occurring minerals in bone. In particular, there remains a need to provide synthetic bone materials which are completely bioresorbable, poorly-crystalline, nanometer-sized crystals which can be formed at low temperatures.

SUMMARY OF THE INVENTION

It is the object of the present invention to provide a specific process that converts standard inert amorphous calcium phosphate into a highly reactive amorphous calcium phosphate.

It is the object of the present invention to provide this reactive amorphous calcium phosphate with particle surfaces that mimic the surface reactivity of naturally-occurring bone mineral.

It is the object of the present invention to provide this reactive amorphous calcium phosphate material which can be used as a reactant with other calcium phosphate solids to form a nano-sized, poorly-crystalline hydroxyapatite solids with Ca/P ratios comparable to naturally occurring bone minerals.

It is the object of the present invention to provide a reactive amorphous calcium phosphate material that is capable of reacting completely and homogeneously with other calcium phosphate solids to form a nano-size, poorly-crystalline hydroxyapatite solids with Ca/P ratios comparable to naturally occurring bone minerals.

It is yet another object of the present invention to provide this reactive amorphous calcium phosphate, when reacted with other calcium phosphates, is capable of forming poorly-crystalline hydroxyapatite at low temperatures (at body temperature of 37° C.).

It is yet a further object of the present invention to provide an injectable calcium phosphate mixture.

In one aspect of the present invention, a method for obtaining a reactive amorphous calcium phosphate is provided. According to the method of the invention, an amorphous calcium phosphate is precipitated from an aqueous solution comprising calcium ions, phosphate ions and carbonate ions, so as to obtain an amorphous carbonated calcium phosphate having a calcium to phosphorous ratio in a range of about 1.55 to 1.7, and alternatively in a range of about 1.55 to 1.65, and alternatively in a range of about 1.55 to 1.6. The amorphous carbonated calcium phosphate is then freeze-dried under conditions selected to maintain the amorphous character of the calcium phosphate. The dried amorphous carbonated calcium phosphate then is heated under conditions selected to remove residual water and carbonate, to obtain a reactive amorphous calcium phosphate having a calcium to phosphate ratio in the range of about 1.55 to 1.7, and alternatively in the range of about 1.55 to 1.65, and alternatively in the range of about 1.55 to 1.6.

In preferred embodiments, vacant reactive sites are introduced into the amorphous carbonated calcium phosphate during the drying step. In other preferred embodiments, the calcium to phosphate ratio is about 1.58. The precipitation may be carried out at a pH greater than 8. In other preferred embodiments, a bone regenerative protein or an antibiotic may be added to the amorphous carbonated calcium phosphate prior to drying.

The step of drying the amorphous calcium phosphate may include lyophilization of the amorphous calcium phosphate. The step of heating may include heating at a temperature sufficient to reduce the carbonate content of the amorphous calcium phosphate, but insufficient to destroy the amorphous character of the calcium phosphate. In other preferred embodiments, heating is carried out at a temperature in the range of about 450°–500° C. Heating may also be carried out under a vacuum at a temperature in the range of 60 to 400° C., and preferably at a temperature in the range of about 175°–225° C.

Another aspect of the invention includes a reactive amorphous calcium phosphate material having the composition of comprising a Ca/P ratio in the range of about 1.55 to 1.7, and alternatively in the range of about 1.55 to 1.65, and alternatively in the range of about 1.55 to 1.6. The amorphous calcium phosphate comprises vacant reactive sites and is well characterized by x-ray diffraction and infrared spectroscopy. The reactive amorphous calcium phosphate may include reactive vacant sites, the reactive sites obtainable upon removal of an ionic pre-component of the amorphous calcium phosphate by thermal decomposition of the pre-component into gaseous or vaporous by-products. In preferred embodiments, the Ca/P ratio is about 1.58.

In another aspect of the invention, a method for preparing a poorly crystalline hydroxyapatite is provided. The method includes providing a reactive amorphous calcium phosphate material having a calcium to phosphate ratio in the range of about 1.55 to 1.7, and alternatively aobut 1.55 to 1.65, and alternatively about 1.55 to 1.6, and reactive vacant sites, and mixing the reactive amorphous calcium phosphate with an aqueous mixture or slurry of a second calcium phosphate. The second calcium phosphate and amorphous calcium phosphate present are in a proportion to provide a Ca/P ratio characteristic of a hydroxyapatitic calcium phosphate.

In preferred embodiments, the Ca/P ratio of the reactive amorphous calcium phosphate is about 1.58 and the Ca/P ratio of poorly crystalline hydroxyapatite is in the range of 1.55 to 1.68. In other preferred embodiments, the second calcium phosphate is selected from the group consisting of dicalcium phosphate dihydrate, $Ca(PO_3)_2$ (calcium metaphosphates), $Ca_7(P_5O_{16})_2$ (heptacalcium phosphate), $Ca_2P_2O_7$ (calcium pyrophosphate) and $Ca_3(PO_4)_2$ (tricalcium phosphates). The second calcium phosphate powder is amorphous or microcrystalline. The method may include the additional step of adding a bone regenerative protein or an antibiotic to the mixture.

Another aspect of the invention includes an injectible paste having a mixture of a reactive amorphous calcium phosphate powder, the amorphous calcium phosphate having a calcium to phosphorous atomic ratio in the range of about 1.55 to 1.70, and alternatively about 1.55 to 1.65, and alternatively 1.55 to 1.6, and reactive vacant sites, and a second calcium phosphate powder, and an amount of water sufficient to provide the desired consistency. The water is buffered to a physiologically acceptable pH. The paste is hardenable at body temperature.

In preferred embodiments, the second calcium phosphate is selected from the group consisting of $CaHPO_4 \cdot 2H_2O$ (dicalcium phosphate dihydrate), $Ca(PO_3)_2$ (calcium metaphosphates), $Ca_7(P_5O_{16})_2$ (heptacalcium phosphate), $Ca_2P_2O_7$ (calcium pyrophosphate) and $Ca_3(PO_4)_2$ (tricalcium phosphates). The second calcium phosphate powder may be amorphous or microcrystalline. The paste may additionally include a bone regenerative protein or an antibiotic.

In yet another aspect of the invention, a method for promoting bone growth is provided. The method includes identifying a site requiring bone growth and applying to the site a mixture of a reactive amorphous calcium phosphate powder, the amorphous calcium phosphate having a calcium to phosphorous atomic ratio in the range of about 1.55 to 1.70, and preferably about 1.55 to 1.65, and alternatively about 1.55 to 1.6, and reactive vacant sites, and a second calcium phosphate powder in an amount of water sufficient to provide the desired consistency. The mixture is allowed to harden. The method may additionally include the addition of a bone regenerative protein or an antibiotic to the mixture prior to application.

"Highly reactive" is used herein to refer to the reactivity of the amorphous calcium phosphate of the present invention with other calcium phosphates. The reactivity is characterized by completeness of reaction, the rate of reaction, homogeneity of the resultant product and ability to react with otherwise inert compounds.

BRIEF DESCRIPTION OF THE DRAWINGS

A description of the invention is made with reference to the figures in which:

FIG. 4 is a solubility curve of a poorly crystalline hydroxyapatite product derived from amorphous calcium phosphate of the present invention when compared with a crystalline hydroxyapatite. Note the relative higher solubility of the material of the present invention versus a more crystalline form of hydroxyapatite, as measured by the amount of calcium ions released into solution at 37° C.

DETAILED DESCRIPTION OF THE INVENTION

Figure 1:
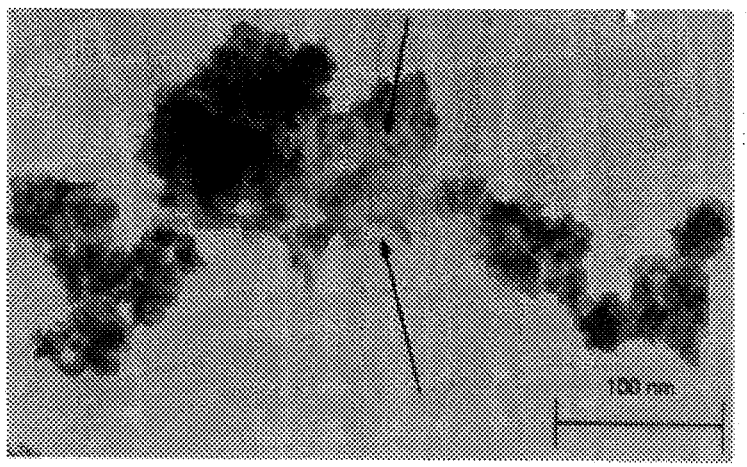
FIG. 1 is a high-resolution transmission electron micrograph of the reactive amorphous calcium phosphate illustrating the nanometer-sized grains in clusters with relatively unclear boundaries and partially immersed in shapeless form (arrows).

The present invention provides a novel process for converting a standard inert amorphous calcium phosphate precipitate into highly reactive amorphous solids. The amorphous solids can be used to react with other calcium phosphate solids to form a poorly-crystalline synthetic hydroxyapatite that provides both bioactivity and structural integrity. This novel amorphous material can be reacted with other calcium phosphates at or below 37° C. to form a bone-like material consisting of poorly crystalline hydroxyapatite.

The amorphous calcium phosphate of the present invention is highly reactive towards other acidic or basic calcium phosphates. Also, the amorphous calcium phosphate of the present invention is considered reactive in that it is capable of reacting at room temperature with a variety of calcium or phosphorus bearing compounds which are conventionally considered "inert", for example CaO. Prior art acid-base reactions of conventional crystalline calcium phosphate results in poorly reacted solids, having reaction product that are too crystalline to be sufficiently soluble in a living tissues. The reactions from prior art are generally incomplete and the reaction products are inhomogeneous. In contrast, the amorphous calcium phosphate of the present invention reacts quickly and completely with a wide variety of calcium phosphates and other calcium or phosphorus bearing materials to provide a homogeneous product.

The source of the enhanced reactivity is not completely understood; however, it is believed to be associated with the amorphicity (lack of crystallinity) and site vacancies in the material, as created by the process of the present invention. The vacancies may provide reactive sites for subsequent reaction. These observations will be discussed more fully, below.

The method of the present invention permits initial formation of amorphous calcium phosphate particles of less than nanometer-sized dimensions, the further growth of which are curtailed by rapid precipitation of the product from solution. During precipitation, certain chemical compositions consisting of, for example, $CO_3^{2-}$ ions, are introduced in the solution so that these ions are incorporated in the amorphous precipitate structure instead of trivalent $PO_4^{3-}$ group(s). Because some $PO_4^{3-}$ is replaced by $CO_3^{2-}$ the overall $PO_4^{3-}$ decreases, thus increasing the Ca/P ratio of the amorphous precipitate (as compared to standard amorphous calcium phosphate) and modifying the valance or charge state of the calcium phosphate. The amorphous solids are then rapidly freeze-dried to preserve the chemical and physical properties of the material. The amorphous solids are then treated under specific temperature and pressure conditions selected to promote the removal of $CO_3^{2-}$ as gaseous carbon dioxide and oxygen from the amorphous solid, while maintaining the amorphicity. The resultant material is an amorphous solid with a higher Ca/P ratio than is typically found in amorphous calcium phosphates, which is generally reported in the past to be 1.50. Further, driving off $CO_3^{2-}$ from the material results in a vacancies in the interstitial structure within the amorphous solids, rendering it a highly reactive solid. It is desirable to maintain the amorphous property of the material throughout the entire process. If crystallinity in its entirety (single crystalline regions) or even in local domains (microcrystalline regions) is introduced during the process or in the final product, the solid has been found to lose its reactivity. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

The amorphous state is induced by controlling the rate and duration of the precipitation process. The amorphous hydroxyapatite of the present invention is precipitated from solution under conditions where initial precipitation is rapid. Rapid precipitation results in the formation of many extremely small calcium phosphate nuclei. Additionally, rapid crystal or grain growth leads to the production of more defects within each grain, thereby also increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to poorly crystalline hydroxyapatite.

The amorphous calcium phosphate solids acquired by this method can be mixed and reacted with other solids or solutions containing phosphates, to obtain solids containing a homogeneous distribution of nanometer-sized crystals. Further, because the amorphous calcium phosphate reacts completely with the other solids, the Ca/P of the resultant solid will constitute the total calcium and phosphorous from such reaction, i.e., there will be complete reaction. When a proper molar concentration of phosphate from the solution or solids is reacted with the novel amorphous calcium phosphate material, a hydroxyapatite material (Ca/P 1.55–1.70) is obtained. Thus, the present invention permits one to design and modify the chemical composition of the resultant product, thereby providing a further mode of controlling bioactivity of the final product used as bone graft material.

The bioactivity of the synthetic bone graft material of the present invention is enhanced relative to standard crystalline hydroxyapatite due to its controlled solubility in the patient. Desirably, a bone graft of poorly-crystalline hydroxyapatite is capable of resorbing at an optimum rate for bone to grow in and replace it. The solubility of poorly-crystalline hydroxyapatite can be varied by modifying the Ca/P chemical composition and/or the nano-sized crystal microstructure, which can be controlled as described herein. In general, poorly-crystalline solids are more soluble than the comparable crystalline solid. By being able to control the solubility of the final product used as bone graft material, one can design the composition of the material to biocorrespond for younger, older or different bony site applications.

In one embodiment of the present invention, a solution is prepared which contains calcium and phosphate ions in a concentration, at a pH and at a temperature which will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to insure that an amorphous compound is obtained.

The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor nonstable phases as a product. Allowing more reaction time for each ions to juxtaposition correctly to form a solid will result in a more thermodynamically favored crystalline and stable structure.

Preferred calcium and phosphate sources: The use of highly concentrated or near supersaturation solutions ensures a more rapid reaction to occur.

Preferred temperature: Although the reaction can be carried out at room temperature, temperatures of near boiling point to increase the concentration of one reactant is a possible means of increasing the rate of reaction.

Preferred pH: Relatively alkaline range of greater than pH 8 is generally used in the reaction.

In a preferred embodiment, a carbonated amorphous calcium phosphate is formed initially. An aqueous solution of calcium ions, phosphate ions and carbonate ions are mixed together rapidly to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution.

Use of a carbonated material is desirable because it permits manipulation of the Ca/P ratio by substitution of $PO_4^{3-}$ by $CO_3^{2-}$. Is recognized, however, that other ions may be suitable in place of or in addition to carbonate ion in modifying the Ca/P ratio and in introduction of reactive site vacancies into the amorphous calcium phosphate, such as by way of example only, nitrate and nitrite ions.

The amorphous calcium phosphate precipitate is collected and filtered immediately. It is preferred to perform this step in a cold room or at subambient temperatures so as to preserve the amorphous state of the precipitate collected. Collection may typically be carded out by any conventional means, including, but in no way limited to gravity filtration, vacuum filtration or centrifugation. The collected precipitate is gelatinous and is washed more than once with distilled water.

The washed precipitate is then immediately freezed, for example but not limited to, by submerging into liquid nitrogen. Upon freezing, precipitate while kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-3}$–$10^{-5}$ torr. A preferred method includes lyophilization because the cryogenic temperatures typically used in lyophilization inhibit further crystallization of the material. As a result, the amorphous calcium phosphate obtained thereby is an extremely fine free flowing powder.

In a subsequent heat treatment of the dried amorphous calcium phosphate, the powder is heated to drive off remaining free water, water of hydration and to decompose $CO_3^{2-}$ into $CO_2$ and oxygen. The heating step is carried out at a temperature of less than 500° C. but more than 425° C., so as to prevent conversion of the amorphous calcium phosphate into crystalline hydroxyapatite. Heating is preferably carried out at a temperature in the range of 450°–460° C. In a preferred embodiment, the freeze-dried amorphous calcium phosphate powder is heated under vacuum. In a vacuum environment, the temperature may be considerably less, i.e., in the range of about 175°–225° C., to obtain the same result. The lower temperatures may be desirable because they reduce the risk of crystallization of the amorphous powder.

Low crystallinity and site vacancies have been associated with the observed higher reactivity of the amorphous calcium phosphate of the present invention. This is exemplified by the following observations. An amorphous calcium phosphate which has been heated to 525° C. is observed to have an increase in formation of crystalline hydroxyapatite and to have a corresponding decrease in reactivity. An amorphous calcium phosphate that is heated to 400° C. retains its amorphous characteristic, but also has a significant carbonate content (as observed by Infrared Spectroscopy). The material also exhibits a corresponding decrease in reactivity. This suggests that both amorphicity and vacant reactive sites are a factor in reactivity. This is not intended to be in any way an exclusive basis for reactivity. Other basis for the observed reactivity are considered to be within the scope of the invention.

The resulting amorphous calcium phosphate powder is a highly reactive amorphous calcium phosphate material with a Ca/P ratio of between 1.55 to 1.65, and preferably 1.58. The powder has been characterized by a variety of analytical techniques.

Figure 2:
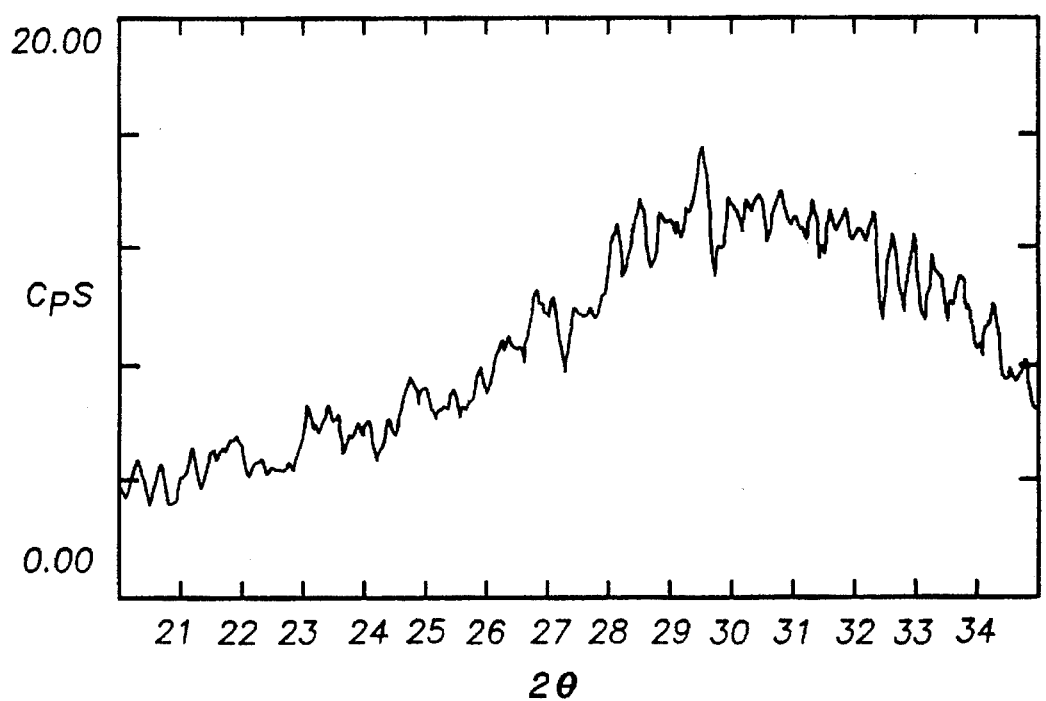
FIG. 2 is an x-ray diffraction pattern of the reactive amorphous calcium phosphate of the present invention (a) prior to and Co) after the vacuum heating step. The material is showing the preservation of the amorphous state after the vacuum heat treatment. It is characterized by absence of sharp peaks and broad maxima between 20° and 35° diffraction angle. The amorphous state of the solids is maintained throughout the entire process of the present invention.
Figure 2:
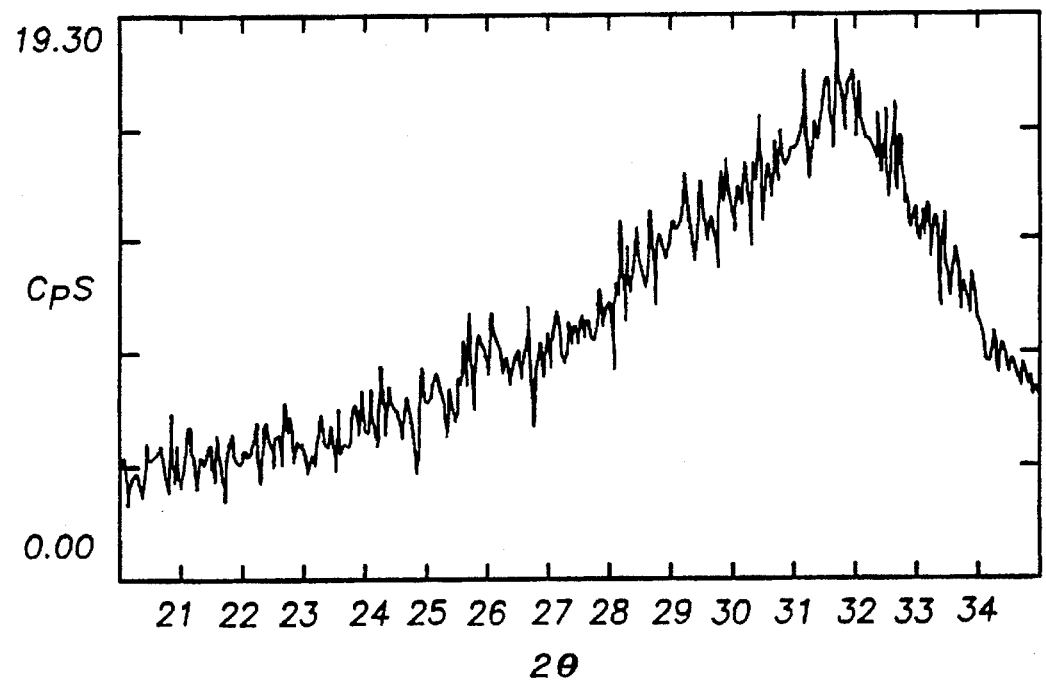
Figure 3:
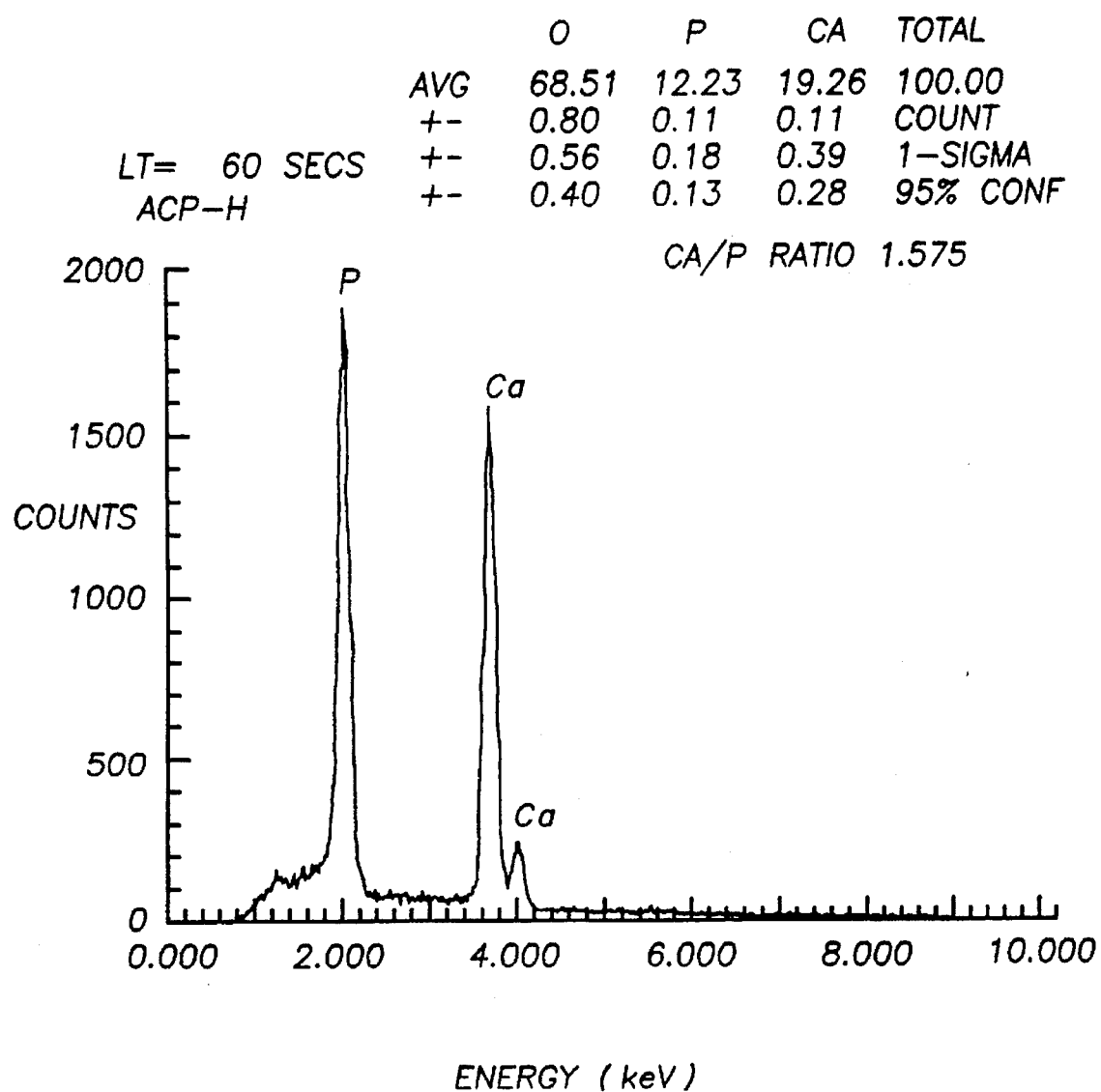
FIG. 3 is an energy-dispersive electron microprobe spectrum of the reactive amorphous calcium phosphate of the present invention after the vacuum heating procedure which yielded Ca/P to be 1.58.

In FIG. 1, a high-resolution transmission electron micrograph is shown to illustrate the morphological characteristics and the nanometer-sized nature of the reactive amorphous calcium phosphate of the present invention. Note the unclear boundaries separating the globule-like clusters, lacking clear edges and surfaces, in contrast to crystalline materials. The x-ray diffraction patterns in FIG. 2 of the same materials show that (a) the amorphous state after the lyophilization is unchanged after the (b) vacuum heat treatment. The amorphous nature of the present invention material is characterized by broad peaks and undefined background with absence of sharp peaks at any position of the diffracting angles. The Ca/P measurement performed using energy-dispersive electron micro-probe of the same material after vacuum heat treatment yields Ca/P to be 1.58 (FIG. 3).

These characterizations using various analytical techniques demonstrate that although there is a change in the local moiety of certain groups in the amorphous calcium phosphate solids, the overall amorphicity is maintained throughout the process. Thus allowing an interpretation of the material to contain local vacancies or "holes" in the amorphous structure which may render it to be a reactive state. This is further evidenced in FIG. 4 where the amorphous calcium phosphate material of the present invention is tested for solubility in comparison with a more crystalline form of hydroxyapatite. The solubility, thus the ability to resorb in a living tissue, is significantly higher in the material of the present invention than the conventional crystalline form of hydroxyapatite.

In another preferred embodiment, the highly reactive amorphous calcium phosphate is reacted with an acidic or basic calcium phosphate, depending on the Ca/P ratio of the reactive amorphous material used, to obtain a poorly crystalline hydroxyapatite. As discussed above, hydroxyapatite is the thermodynamically preferred reaction product which readily crystallizes to give a product that is not biocompatible due to its insolubility under physiological conditions. The use of an amorphous calcium phosphate, which can react quickly and completely to a product hydroxyapatite without significant crystallization, provides a novel route to a poorly-crystalline hydroxyapatite which is resorbable under physiological conditions.

The amorphous calcium phosphate powder of the present invention may be mixed with a variety of calcium phosphate powders to thereby react to form a poorly crystalline form of hydroxyapatite. This reaction occurs at room temperature upon mixing of the powder with the calcium phosphate in the presence of water or a buffer solution. Depending upon the amount of water added the mixture of amorphous calcium phosphate of the present invention and acidic calcium phosphate results in a highly formable and/or highly injectable paste with varying degrees of paste consistency.

Appropriate calcium phosphates include both basic and acidic calcium phosphates which provide the appropriate stoichiometry for reaction to obtain a hydroxyapatitic calcium phosphate. In a preferred embodiment, an acidic calcium phosphate is used. Suitable acidic calcium phosphates include, but are in no way limited to, calcium metaphosphate, dicalcium phosphate dihydrate, heptacalcium phosphate, tricalcium phosphates, calcium pyrophosphate dihydrate, calcium pyrophosphate, and octacalcium phosphate. Other solids which would provide the source for phosphate or calcium, corresponding appropriately to the Ca/P ratio of the reactive amorphous calcium of the present invention used, may be mixed to form a final product which would yield desired Ca/P ratio close to natural bone. It may be desirable to provide the second calcium phosphate in the amorphous or microcrystalline state, as well.

Because at least one of the reactants is amorphous and highly reactive, the reaction proceeds at room temperature to provide an apatitic material having a poorly-crystalline or microcrystalline microstructure. The reaction also is substantially complete, thereby insuring that all calcium and phosphate of the mixture are consumed by the resultant hydroxyapatite product. This permits reliable manufacture of hydroxyapatite products simply by selection of the relative proportions of the starting amorphous and secondary calcium phosphates. It is desirable to maintain a calcium to phosphate ratio of about 1.5–1.68 because naturally occurring minerals in human bone are within this range.

The product hydroxyapatite material contains labile environments characteristic of naturally-occurring bone. In naturally occurring bone, minerals are characterized by nanometer-sized structure, providing high surface areas to interact with the surrounding tissue environment, resulting in resorption and remodelling of tissues. The present invention, with its nanometer-sized crystals as the product, closely mimics the naturally occurring bone minerals. Further, properties such as crystallinity and Ca/P ratios are closely designed in the present invention to simulate the mineral properties found in living tissues of bone.

In another preferred embodiment, an injectable paste may be prepared, which can be introduced into the bone repair site. The paste is prepared by mixture of the amorphous calcium phosphate of the present invention with a second calcium phosphate in an amount of water or buffer sufficient to produce the desired consistency for injection. Because of the amorphous nature of the component solids in the paste, the material has markedly improved flow characteristics over prior art compositions. Flow characteristics of the resultant paste are toothpaste-like while prior art materials inherits a granular or oat meal-like consistency. The paste may be prepared before use, up to period of several days. The storage time of the paste may be extended by maintaining paste at reduced temperatures in the range of 1°–10° C. in the refrigerator.

In another embodiment of the invention, it is contemplated to incorporate bone regenerative proteins (BRP) into the amorphous calcium phosphate and acidic calcium phosphate mixture. BRPs have been demonstrated to increase the rate of bone growth and accelerate bone healing. A bone graft including nanocrystalline or poorly crystalline hydroxyapatite and BRP is expected to promote bone healing even more rapidly than a bone graft using the hydroxyapatite of the present invention alone. The efficacy of BRP is further enhanced by controlling the solubility of the nanocrystalline or poorly crystalline hydroxyapatite such that it dissolves at a rate that delivers BRP, calcium, and phosphorus at the optimum dosage for bone growth. Such a method of incorporating BRP would include, but not limited to, mixing a buffer solution containing BRP with its optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenetic Proteins. Such BRPs are currently being developed by Genetics Institute, Cambridge, Mass.; Genentech, Palo Alto, Calif.; and Creative Biomolecules, Hopkinton, Mass.

In another embodiment of the invention, it is contemplated to incorporate antibiotics or its agents into the amorphous calcium phosphate and its mixture. From a clinical sense, one of the major implication arising from a bone-graft surgery is a need to control the post-operative inflammation or infection. A bone graft including poorly crystalline hydroxyapatite and antibiotic(s) is expected to reduce the chances of local infection at the surgery site, contributing to infection-free, thus faster bone healing process. The efficacy of antibiotics is further enhanced by controlling the release of the poorly crystalline hydroxyapatite such that it dissolves at a rate that delivers antibiotic peptides or its active component at the most effective dosage to the tissue repair site. Exemplary antibiotics include, but are in no way limited to, Penicillin, Chlortetracycline hydrochloride (Aureomycine), Chloramphenicol and Oxytetracycline (Terramycine). Both antibiotics, mostly polypeptides, and bone regenerating proteins may be intermixed with the poorly crystalline hydroxyapatite material of the present invention, to locally deliver all or most of the necessary components in facilitating optimum condition for bone tissue repair.

EXAMPLES

The invention is further exemplified with reference to the following examples, which are presented for the purpose of illustration only and are not to be considered as limiting of the invention.

Example 1. This example describes the step-by-step preparation and methods to render relatively inert amorphous calcium phosphate solids into a highly reactive amorphous calcium phosphate of the present invention.

Solution A is prepared at room temperature by the rapid dissolution of 55 g NaHPO$_4$ (sodium phosphate), 50 g NaOH (sodium phosphate), 30 g NaHCO$_3$, (sodium bicarbonate).

Solution B is prepared at room temperature by rapid dissolution of 43 g Ca(NO$_3$)$_2$.4H$_2$O (calcium nitrate tetrahydrate).

The inert carbonated amorphous calcium phosphate is then prepared at room temperature by the rapid addition of solution B to rapidly stirring solution A. Precipitate of a gel-like amorphous calcium phosphate is formed and is immediately filtered using filter paper with medium filter speed and a vacuum pressure of about 10$^{-2}$ torr. After forming a thin cake, the material is washed with approximately 4 liters of distilled water by adding water into the flitrating funnel. The washed material is then collected using spatula and immersed into a liquid nitrogen in 200 ml container. Once the precipitate forms into hard frozen pieces, the container is transferred into a vacuum chamber for 24 hrs (10$^{-3}$ torr), until fine and dry powder is obtained.

Although the procedure described above may be performed in room temperature, the entire process preferably takes place in below ambient temperature (4°–5° C.) room, so as to further preserve the amorphous state from converting into more stable crystalline form. Further, such elements or ions known to act as inhibitors of crystalline hydroxyapatite formation may be added into the solution in trace amounts. These may be, for example, Mg ions in the form of less than 0.5 g MgCl$_2$.6H$_2$O (magnesium chloride), pyrophosphate ions in the form of less than 1 g Na$_4$P$_2$O$_7$—10H$_2$O (sodium pyrophosphate).

An infrared spectrum of the inert amorphous material at this point in process is shown in FIG. 2a. This spectrum contains peaks characteristic of P—O groups (600 and 1000 cm$^{-1}$), CO$_3^{2-}$ group (1,630 cm$^{-1}$) with relatively large peak of O—H group (~3,550 cm$^{-1}$). X-ray diffraction pattern of the inert amorphous materia (FIG. 2a) show amorphous nature of the material as demonstrated by absence of any sharp peaks when the measurement of crystallinity is determined by taking ratio of coherent peaks to background.

The inert amorphous material described above is then made into a reactive form by heating for 80 minutes at 455° C. (±3° C.). Note, however, that the amorphous nature of the material is not lost during this process, as demonstrated by the x-ray diffraction pattern shown in FIG. 2(b). The Ca/P ratio measurement of this material after the heat treatment was determined to be 1.575, using a method of quantitative electron microprobe analysis (FIG. 3). The overall morphological and ultrastructural properties of amorphous material is shown in FIG. 1, as seen under a transmission electron microscope. Note the "amorphous" appearance of the material with absence of sharp edges separating each granules with certain portion of the material to exhibit shapeless form (arrows).

Example 2: Procedures as described in Example 1 above, but replacing the preparation of Solution A and B by the following reactions. Solution A is prepared at room temperature by the rapid dissolution of 90.68 g of Ca(NO$_3$)$_2$..4H$_2$O in 1.2 liter of carbonated distilled H$_2$O. Solution B is prepared by using 40.57 g of K$_2$HPO$_4$ in 1.53 liters of distilled H$_2$O, plus 24 ml of 45 vol. % KOH solution. Chemical and physical properties resulting from this procedure results in an amorphous material analogous to the characteristics presented for Example 1.

Example 3: Procedure as described in Example 1 above, but replacing the preparation of Solution A and B by the following reactions. Solution A is prepared at room temperature by the rapid dissolution of 10.58 g of Ca(NO$_3$)$_2$.6H$_2$O in 0.15 liters of carbonated distilled H$_2$O at pH greater than 9.0, as adjusted by NaOH. Solution B is prepared by dissolving 7.8 g of (NH$_4$)$_2$HPO$_4$ in 0.35 liters of distilled H$_2$O. Chemical and physical properties resulting from this procedure results in an amorphous material analogous to the characteristics presented in Examples 1 and 2.

Example 4: Reactive amorphous calcium phosphate material prepared from Examples 1, 2, or 3 is physically dry-mixed with dicalcium phosphate dihydrate ($CaHPO_4 \cdot 2H_2O$) at 50:50 wt. % using rolling mill for 24 hrs. Water (2 ml/g of mixed material) is then added to the powder mixture to yield a paste-like consistency. Amount of $H_2O$ added may vary depending on whether thick or thin paste is desired. The paste material is then placed in moist tissue environment where upon reaching body temperature (37° C.), hardens into a solid mass without exothermic behavior. The hardening process may be delayed for up to several days by placing it into a refrigerating temperature of 4° C. The hardened material is composed of nanometer-sized, poorly crystalline hydroxyapatite with inherent solubility property that exceeds higher than ever reported for a synthetic hydroxyapatite material. This is demonstrated in FIG. 4, where the concentration of calcium ions released into a controlled pH buffer solution over 24 hrs at 37° C., is significantly higher for the material of the present invention than the standard crystalline hydroxyapatite material.

Example 5: This example describes the preparation of dicalcium phosphate dehydrate for use in a reaction with amorphous calcium phosphate described in Example 4 above.

Solution A is prepared at room temperature by the rapid dissolution of 17.1 g $Ca(NO_3)_2 \cdot 4H_2O$ (calcium nitrate tetrahydrate) in 250 ml distilled water. Solution B is prepared at room temperature by rapid dissolution of 10 g $H_9N_2O_4P$ (diammonium hydrogen phosphate) in 500 mL distilled water at a pH of 4.6–4.8.

The dicalcium phosphate dihydrate is prepared at room temperature by the rapid addition of solution B to the stirring solution A. Immediately after this, the sample is filtered using filter paper with medium filter speed and a vacuum pressure of about $10^{-2}$ torr. After forming a thin cake, the material is washed with about 2 liters of distilled water. The washed material is then dried at room temperature for 24–72 hrs.

Example 6: Reactive amorphous calcium phosphate material prepared in Examples 1,2, or 3 are dry-mixed with other calcium phosphate compound, other than dicalcium phosphate dihydrate reported in Example 4. These compounds include, but not limited to: $Ca(PO_3)_2$ (calcium metaphosphates), $Ca_7(P_5O_{16})_2$ (heptacalcium phosphate), $Ca_2P_2O_7$ (calcium pyrophosphate), $Ca_3(PO_4)_2$ (tricalcium phosphates). If dry-mixture ratio, depending on the molar Ca/P ratio of the compound mixed with the reactive amorphous calcium, is properly calculated to be between Ca/P ratios of 1.5–1.70, the resulting material is poorly crystalline hydroxyapatite solids with solubility properties same as shown in FIG. 4.

Example 7: This example describes the preparation of an injectable paste for the formation of poorly crystalline hydroxyapatite solid.

The dried mixed materials prepared according to Examples 4 or 6, are mixed with distilled $H_2O$ (2.3 ml/g). A paste is formed that can be easily shaped by hand or injected through a nozzle as small as 0.5 mm ID. The flowability increases after refrigerating the paste at 4° C. for 2–3 hrs.

The material can be stored in a paste form for approximately one week at 4° C. in an air tight container without hardening.

Example 8: This example describes the preparation of an injectable paste for the formation of poorly crystalline hydroxyapatite solid with protein or polypeptide (i.e., Bone regenerating protein, Antibiotics) component(s) added to the mixture.

The procedure requires instead of using distilled $H_2O$ as described in Example 7, a buffer solution with optimum pH range for the protein or peptide bioactivity is used.

It will be understood that the objects set forth above, among those made apparent from the preceding description, are efficiently attained and, since certain changes may be made in carrying out the above process and in the composition set forth without departing from the spirit and scope of the invention, it is intended that all matter contained in the above description and shown in the accompanying drawing (s) shall be interpreted as illustrative and not in a limiting sense.

It will be further understood that the following claims are intended to cover all of the generic and specific features of the invention herein described, and all statements of the scope of the invention which might be said to fall therebetween.

What is claimed is:

1. A method of preparing a poorly crystalline hydroxyapatite, comprising:

providing a carbonated amorphous calcium phosphate material;

removing at least a portion of the carbonate component from the carbonated amorphous calcium phosphate by thermal decomposition to form a decarbonated amorphous calcium phosphate;

combining the decarbonated amorphous calcium phosphate and a second calcium phosphate in an aqueous medium without exothermic behavior, the second calcium phosphate and amorphous calcium phosphate present in a proportion to provide a Ca/P ratio characteristic of an apatitic calcium phosphate, whereby a hardened poorly crystalline hydroxyapatite is formed.

2. The method of claim 1, wherein the second calcium phosphate is selected from the group consisting of $CaHPO_4 \cdot 2H_2O$ (dicalcium phosphate dihydrate), $Ca(PO_3)_2$ (calcium metaphosphates), $Ca_7(P_5O_{16})_2$ (heptacalcium phosphate), $Ca_2P_2O_7$ (calcium pyrophosphate) and $Ca_3(PO_4)_2$ (tricalcium phosphates).

3. The method of claim 1, wherein the second calcium phosphate powder is amorphous or microcrystalline.

4. The method of claim 1, further comprising: adding a bone regenerative protein to the mixture.

5. The method of claim 1, further comprising:

adding an antibiotic to the mixture.

6. The method of claim 1, wherein the carbonated amorphous calcium phosphate material is obtained by precipitating a carbonated amorphous calcium phosphate from an aqueous solution comprising calcium ions, phosphate ions and carbonate ions and the thermal decomposition comprises heating the carbonated amorphous calcium phosphate under conditions which retain the amorphous character of the calcium phosphate, said conditions selected to remove at least a portion of residual aqueous medium and at least a portion of the carbonate ion.

7. The method of claim 1, wherein the reactive amorphous calcium phosphate and the second calcium phosphate are mixed together prior to addition of the aqueous medium such that no prereaction occurs between the decarbonated amorphous calcium phosphate and the second calcium phosphate prior to addition of the aqueous medium.

8. The method of claim 1, wherein the aqueous medium is buffered to a physiologically acceptable pH.

* * * * *

UNITED STATES PATENT AND TRADEMARK OFFICE
CERTIFICATE OF CORRECTION

PATENT NO. : 5,650,176
DATED : July 22, 1997
INVENTOR(S) : Dosuk D. Lee, Christian Rey, and Maria Aiolova It is certified that error appears in the above-identified patent and that said Letters Patent is hereby corrected as shown below:

In column 1, line 50, replace "has" with --have--;

In column 1, line 58, after "of" insert --the--;

In column 1, line 63, after "bone" insert --will--;

In column 2, line 11, after "that" insert --a--;

In column 2, line 49, replace "discloses" with --disclose--;

In column 2, line 50, after "in" insert --a--;

In column 2, line 54, replace "reactant" with --reactants--;

In column 2, line 57, after "be" insert --an--;

In column 4, line 52, replace "aobut" with --about--;

In column 6, line 64, delete "a".

In column 8, line 35, replace "Is" with --It is--;

In column 11, line 19, after "not" insert --be--.

In column 13, line 34, after "water" replace "," with --.--;

In column 13, line 42, after "but" insert --are--.

UNITED STATES PATENT AND TRADEMARK OFFICE
CERTIFICATE OF CORRECTION

PATENT NO. : 5,650,176
DATED : July 22, 1997
INVENTOR(S) : Dosuk D. Lee, Christian Rey, and Maria Aiolova It is certified that error appears in the above-identified patent and that said Letters Patent is hereby corrected as shown below:

In column 4, line 36, delete "of"

In column 5, line 55, replace "Co)" with --(b)--;

In column 12, lines 23-27, delete "An infrared spectrum of the inert amorphous material at this point in process is shown in FIG. 2a. This spectrum contains peaks characteristic of P—O groups (600 and 1000 cm$^{-1}$), $CO_3^{2-}$ group $(1,630)^{-1}$ with relatively large peak of O—H group (~3,550 cm$^{-1}$)."

Signed and Sealed this

Fifteenth Day of May, 2001

Attest:

NICHOLAS P. GODICI

Attesting Officer

Acting Director of the United States Patent and Trademark Office